United States Patent
Westerhoff et al.

(10) Patent No.: US 12,029,826 B2
(45) Date of Patent: Jul. 9, 2024

(54) UV-C WAVELENGTH SIDE-EMITTING OPTICAL FIBERS

(71) Applicants: Paul K. Westerhoff, Scottsdale, AZ (US); Zhe Zhao, Tempe, AZ (US); Nora Shapiro, Tempe, AZ (US)

(72) Inventors: Paul K. Westerhoff, Scottsdale, AZ (US); Zhe Zhao, Tempe, AZ (US); Nora Shapiro, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 310 days.

(21) Appl. No.: 17/667,283

(22) Filed: Feb. 8, 2022

(65) Prior Publication Data
US 2022/0249719 A1 Aug. 11, 2022

Related U.S. Application Data (60) Provisional application No. 63/146,972, filed on Feb. 8, 2021.

(51) Int. Cl.
*A61L 2/10* (2006.01)
*C03C 25/00* (2018.01)
(Continued)

(52) U.S. Cl.
CPC .............. *A61L 2/10* (2013.01); *C03C 25/105* (2013.01); *C03C 25/305* (2013.01);
(Continued)

(58) Field of Classification Search
CPC ...... A61L 2/10; A61L 2202/11; C03C 25/105; C03C 25/305; C09D 147/00; G02B 6/0006; G02B 6/001
See application file for complete search history.

(56) References Cited

U.S. PATENT DOCUMENTS

| 5,637,877 A | 6/1997 | Sinofsky |
| 5,905,837 A | 5/1999 | Wang |

(Continued)

FOREIGN PATENT DOCUMENTS

| CN | 1612754 | 5/2005 |
| ES | 2673673 | 6/2018 |

(Continued)

OTHER PUBLICATIONS

Bagwe et al., "Surface modification of silica nanoparticles to reduce aggregation and nonspecific binding," Langmuir. Apr. 25, 2006, 22(9):4357-62.

(Continued)

*Primary Examiner* — Nicole M Ippolito
(74) *Attorney, Agent, or Firm* — Fish & Richardson P.C.

(57) ABSTRACT

A coated optical fiber includes an optical fiber having a core and an outer surface, and a homogeneous polymer coating in contact with the outer surface of the optical fiber. The optical fiber and the homogeneous polymer coating are UV transparent, and a refractive index of the outer surface of the optical fiber or the homogeneous polymer coating is up to 15% less than a refractive index of the core. Coating the optical fiber includes coating an outer surface with a polymerizable material and polymerizing the polymerizable material to yield the coated optical fiber having a homogeneous polymer coating. The optical fiber and the homogeneous polymer coating are UV transparent, and a refractive index of the outer surface of the optical fiber or the homogeneous polymer coating is up to 15% less than a refractive index of a core of the optical fiber.

22 Claims, 7 Drawing Sheets

(51) Int. Cl.
- *C03C 25/105* (2018.01)
- *C03C 25/305* (2018.01)
- *C09D 147/00* (2006.01)
- *F21V 8/00* (2006.01)
- *G02B 6/00* (2006.01)

(52) U.S. Cl.
CPC ......... *C09D 147/00* (2013.01); *G02B 6/0006* (2013.01); *G02B 6/001* (2013.01); *A61L 2202/11* (2013.01)

(56) References Cited

U.S. PATENT DOCUMENTS

| | | |
|---|---|---|
| 6,347,172 B1 | 2/2002 | Keller |
| 6,418,252 B1 | 7/2002 | Maitland |
| 6,991,847 B2 | 1/2006 | Padmanabhan et al. |
| 7,566,157 B2 | 7/2009 | Lo |
| 7,834,528 B2 | 11/2010 | Numajiri et al. |
| 8,331,750 B2 | 12/2012 | Deng |
| 8,492,448 B2 | 7/2013 | Dewa |
| 8,929,703 B2 | 1/2015 | Logunov |
| 9,259,513 B2 | 2/2016 | Bedwell |
| 9,304,278 B1 | 4/2016 | Bauco |
| 9,618,672 B2 | 4/2017 | Kuchinisky |
| 10,092,356 B2 | 10/2018 | Griffin |
| 10,175,405 B2 | 1/2019 | Logunov |
| 10,293,065 B2 | 5/2019 | Victor |
| 10,323,183 B2 | 6/2019 | Han et al. |
| 10,471,277 B2 | 11/2019 | Rhodes |
| 10,765,768 B2 | 9/2020 | Victor |
| 10,788,621 B2 | 9/2020 | Li et al. |
| 10,793,449 B2 | 10/2020 | Westerhoff |
| 10,870,798 B2 | 12/2020 | Han et al. |
| 11,754,778 B2 | 9/2023 | Westerhoff et al. |
| 11,760,663 B2 | 9/2023 | Westerhoff et al. |
| 2002/0054744 A1 | 5/2002 | Vanpoulle |
| 2003/0148088 A1 | 8/2003 | Padmanabhan et al. |
| 2005/0074216 A1 | 4/2005 | Irie |
| 2007/0120522 A1 | 5/2007 | Eickhoff |
| 2007/0267966 A1 | 11/2007 | Numajiri et al. |
| 2008/0019657 A1 | 1/2008 | Maitland |
| 2010/0091516 A1 | 4/2010 | Haerle |
| 2010/0233021 A1 | 9/2010 | Sliwa |
| 2011/0052926 A1 | 3/2011 | Nakamura |
| 2012/0228236 A1 | 9/2012 | Hawkins, II |
| 2012/0321265 A1 | 12/2012 | Terruzzi |
| 2014/0063838 A1* | 3/2014 | Kouzmina ............... C09D 5/18 362/558 |
| 2014/0352801 A1 | 12/2014 | Mcalister |
| 2015/0144802 A1 | 5/2015 | Bauco |
| 2017/0010411 A1 | 1/2017 | Li et al. |
| 2017/0313601 A1 | 11/2017 | Westerhoff |
| 2018/0244992 A1 | 8/2018 | Han et al. |
| 2018/0321440 A1* | 11/2018 | Bilodeau ............... G02B 6/4267 |
| 2019/0192879 A1 | 6/2019 | Zaborsky |
| 2019/0292452 A1 | 9/2019 | Han et al. |
| 2020/0158948 A1 | 5/2020 | Westerhoff |
| 2021/0032130 A1 | 2/2021 | Westerhoff |
| 2021/0079297 A1 | 3/2021 | Han et al. |
| 2021/0122667 A1 | 4/2021 | Westerhoff |
| 2021/0135423 A1* | 5/2021 | Macomber ......... B23K 26/0643 |
| 2022/0091325 A1* | 3/2022 | Akari ................ G02B 6/02033 |
| 2022/0171122 A1* | 6/2022 | Chen ................. G02B 6/02138 |

FOREIGN PATENT DOCUMENTS

| | | |
|---|---|---|
| JP | 2007130029 | 5/2007 |
| KR | 100909102 | 7/2009 |
| WO | 2002057686 | 7/2002 |
| WO | 2009140025 | 11/2009 |
| WO | 2014159874 | 10/2014 |
| WO | 2016197397 | 12/2016 |
| WO | 2018236812 | 12/2018 |
| WO | 2020072339 | 4/2020 |

OTHER PUBLICATIONS

Bayrakceken et al., "Resonance Fluorescence of Fused Silica by the Depopulation of the Ground State," International Journal of Photoenergy, vol. 2012, Article ID 359384, 3 pages, (Year: 2012).

Belz et al., "Optical detection techniques and light delivery with UV LEDs and optical fibres," Journal of Physics: Conference Series, vol. 85, Third International Conference on Optical and Laser Diagnostics (Icolad 2007) May 22-25, 2007, 7 pages.

Bishop [online], "Summer scholar purifies water with fibers," LLNL, Jul. 26, 2017, URL <https://www.llnl.gov/news/summer-scholar-purifies-water-fibers>, 3 pages.

Chen, J., S. Loeb, and J.H. Kim, LED revolution: fundamentals and prospects for UV disinfection applications. Environmental Science-Water Research & Technology, 2017. 3(2): p. 188-202.

Glover et al. [online], "Laser Generated Side-emitting Fibers for Anti-microbial Applications," Jan. 12, 2017, URL <https://www.laserchirp.com/2017/01/laser-generated-side-emitting-fibers-for-anti-microbial-applications/>, 6 pages.

International Search Report and Written Opinion in International Appln. No. PCT/US2019/053733, dated Dec. 11, 2019, 9 pages.

Lanzarini-Lopes et al., "Optical fiber-mediated photosynthesis for enhanced subsurface oxygen delivery," Chemosphere, 2018, 195:742-748.

Lanzarini-Lopes, "Visible and Ultraviolet Light Side-Emitting Optical Fibers Enable Water Purification," Dissertation, Arizona State University, May 2020, 209 pages.

Lanzarini-Lopes, M., et al., Germicidal glowsticks: Side-emitting optical fibers inhibit Pseudomonas aeruginosa and *Escherichia coli* on surfaces. Water Research, 2020. 184 (116191): p. 1-8.

Lanzarini-Lopes, M., et al., Nanoparticle and Transparent Polymer Coatings Enable UV-C Side-Emission Optical Fibers for Inactivation of *Escherichia coli* in Water. Environmental Science & Technology, 2019. 53(18): p. 10880-10887.

Lanzarini-Lopes, M., et al., Particle-modified polymeric cladding on glass optical fibers enhances radial light scattering. Journal of the Optical Society of America B-Optical Physics, 2019. 36(6): p. 1623-1628.

Ling et al., Coupling Light Emitting Diodes with Photocatalyst-Coated Optical Fibers Improves Quantum Yield of Pollutant Oxidation. Environ Sci Technol., 2017, 51(22):13319-13326.

Naqvi et al., "Uniform Thin Films on Optical Fibers by Plasma-Enhanced Chemical Vapor Deposition: Fabrication, Mie Scattering Characterization, and Application to Microresonators," Journal of Lightwave Technology, vol. 36, No. 23, pp. 5580-5586, 1 Dec. 1, 2018.

Rivero et al., "Optical Fiber Sensors Based on Polymeric Sensitive Coatings," Polymers. Mar. 7, 2018; 10(3):280, 26 pages.

Simon, "Optical Fibers for Water Treatment," LLNL, 17-FS-021, 2017, 34 pages.

Spallino et al., "Visible-ultraviolet vibronic emission of silica nanoparticles," Phys. Chem. Chem. Phys., 2014, 16(40):22028-22034.

Suteewong et al., "Highly Aminated Mesoporous Silica Nanoparticles with Cubic Pore Structure," J. Am. Chem. Soc. 2011, 133, 2, 172-175.

Takada et al., "Bactericidal effects of 310 nm ultraviolet light-emitting diode irradiation on oral bacteria," BMC Oral Health (2017) 17:96, 10 pages.

Urrutia et al., "Optical Fiber Sensors Based on Nanoparticle-Embedded Coatings," Journal of Sensors. 2015. 2015:805053. 18 pages.

Bouchet et al., Enhancement and Inhibition of Spontaneous Photon Emission by Resonant Silicon Nanoantennas, Phys. Rev. Applied, Dec. 2016, 6, 064016, 11 pages.

Dai et al., Ultraviolet C irradiation: an alternative antimicrobial approach to localized infections? Expert Rev Anti Infect Ther., Feb. 2012, 10(2):185-195.

Glinka et al., Photoluminescence Spectroscopy of Silica-Based Mesoporous Materials, J. Phys. Chem. B, 2000, 104, 36, 8652-8663.

(56) References Cited

OTHER PUBLICATIONS

Lanzarini-Lopes et al., "Ultra-Violet Emitting Optical Fibers for Water Treatment," 2017 Lawrence Livermore National Laboratory Summer Student Poster Symposium, Livermore, CA, Aug. 2017. LLNL-POST-735252, 1 page.

Pei et al., Tuning surface properties of amino-functionalized silica for metal nanoparticle loading: The vital role of an annealing process, Surface Science, V. 648, Jun. 2016, pp. 299-306.

Polshettiwar et al., (2010), High-Surface-Area Silica Nanospheres (KCC-1) with a Fibrous Morphology. Angew. Chem. Int. Ed., 49:9652-9656.

Ryu et al., Hierarchical mesoporous silica nanoparticles as superb light scattering materials, Chem. Commun., 2016, 52, 2165-2168.

Sterligov, "Scattering and reflection of light by ordered mesoporous silica films," in Frontiers in Optics, OSA Technical Digest Series (Optica Publishing Group, 2005), paper FThT5, 1 page.

\* cited by examiner

UV-C WAVELENGTH SIDE-EMITTING OPTICAL FIBERS

CROSS-REFERENCE TO RELATED APPLICATION

This application claims the benefit of U.S. Patent Application No. 63/146,972 filed on Feb. 8, 2021, which is incorporated herein by reference in its entirety.

STATEMENT OF GOVERNMENT INTEREST

This invention was made with government support under 1449500 awarded by National Science Foundation and under AGR Sep. 26, 2019 awarded by the National Aeronautical & Space Administration. The government has certain rights in the invention.

TECHNICAL FIELD

This invention relates to ultraviolet-C (UV-C) wavelength side-emitting optical fibers for non-chemical germicidal applications.

BACKGROUND

Bacteria, pathogens and biofilms pose health and operational challenges in human support systems. Existing disinfectants typically rely upon chemical oxidants (e.g., chlorine), gaseous oxidants (e.g., ozone), reactive materials (e.g., silver ions), or germicidal ultraviolet (UV) light. Chemical oxidants, gaseous oxidants, and reactive materials rely upon consumables to be effective. Germicidal irradiation with UV light in the 220 to 280 nm wavelength range (UV-C) cleaves DNA, preventing cellular replication and thus bacterial growth.

SUMMARY

This disclosure relates to UV-C wavelength side-emitting optical fibers and systems including these optical fibers for non-chemical germicidal applications. The UV-C light source (e.g., light emitting diodes) is diffuse (e.g., non-collimated) allowing light rays to enter the optical fiber. Controlling the separation distance (e.g., 0 mm to 2 mm) between the diffuse light source and the optical fiber allows tuning of angles at which light rays to enter the optical fiber above and below the critical angle for the optical fiber. The optical fibers typically have a diameter less than about 1 mm (e.g., about 0.25 or 0.5 mm), and may be a single fiber or bundle of fibers. Optical fibers are held in a connector using a UV transparent polymer. The optical fibers can have a textured surface coated with a UV transparent polymer (e.g., a fluorinated polymer). Varying the surface roughness modulates the incident light angle inside the optical fiber and creates more side emission of UV-C light that leaves the fiber, because it allows each light ray to randomly change angle. Using a single coating (e.g., a UV transparent polymer) allows simpler and lower cost manufacturing compared to other designs that require one or more additional surface coating steps.

As used herein, a material that is "UV transparent" in a selected wavelength range typically has an average percent transmission of least 80%, at least 85%, at least 90%, or at least 95% over the selected wavelength range. The UV transparent polymer has a refractive index less than (e.g., up to 15% less than) that of a core of the optical fiber. The interface of the optical fiber with the UV transparent polymer is tuned by the differences in refractive indices to create one type of textured interfacial surface. Another method to modulate side-emission of light out of the fiber is achieved by surface texturing the optical fiber at the interface, using mechanical or chemical processes. The optical fibers are configured to side emit UV-C light (having a wavelength in a range of about 250 nm to about 280 nm) like "glowsticks" from a light emitting diode (LED) source. Multiple fibers can be bundled and optically coupled to a single LED. The fibers have a size and flexibility suitable for bending and placement to allow irradiation of areas (e.g., water tanks and piping) not typically accessible by rigid glass-based mercury-containing UV lamps.

In addition to the embodiments of the attached claims and the embodiments described above, the following numbered embodiments are also innovative.

Embodiment 1 is a coated fiber comprising:
an optical fiber comprising a core and an outer surface; and
a homogeneous polymer coating in contact with the outer surface of the optical fiber,
wherein the optical fiber and the homogeneous polymer coating are UV transparent, and a refractive index of the outer surface of the optical fiber or the homogeneous polymer coating is up to 15% less than a refractive index of the core.

Embodiment 2 is a coated optical fiber of embodiment 1, wherein UV light passing through the optical fiber is scattered by an interface between the outer surface of the optical fiber and the homogenous polymer coating.

Embodiment 3 is a coated optical fiber of embodiment 1 or 2, wherein a thickness of the homogeneous polymer coating is between about 10 μm and about 100 μm.

Embodiment 4 is a coated optical fiber of any one of embodiments 1 through 3, wherein the homogeneous polymer coating comprises a fluorinated polymer.

Embodiment 5 is a coated optical fiber of any one of embodiments 1 through 4, wherein a refractive index of a portion of the optical fiber within 1 μm of the outer surface of the optical fiber is up to 15% less than the refractive index of the core of the optical fiber.

Embodiment 6 is a coated optical fiber of any one of embodiments 1 through 5, wherein the outer surface comprises features having a peak to valley distance between about 1 nm and about 100 nm.

Embodiment 7 is a disinfectant system comprising a coated optical fiber of any one of embodiments 1 through 6.

Embodiment 8 is an apparatus comprising a light source optically coupled to an end of a coated optical fiber of any one of embodiments 1 through 7.

Embodiment 9 is an apparatus of embodiment 8, wherein the light source comprises a light-emitting diode (LED).

Embodiment 10 is an apparatus of embodiment 9, wherein the light source comprises a UV-C LED with a diffuse, non-collimated, light emission pattern.

Embodiment 11 is an apparatus of any one of embodiments 8 through 10, wherein the light source is thermally coupled to a heat sink.

Embodiment 12 is an apparatus of any one of embodiments 8 through 11, wherein the light source and the end of the optical fiber are separated by a distance selected to modulate angles of light rays entering the end of the optical fiber from the light source.

Embodiment 13 is an apparatus of embodiment 12, wherein a volume defined by the distance comprises a UV transparent material.

Embodiment 14 is an apparatus of embodiment 13, further comprising one or more additional optical fibers coupled to the light source.

Embodiment 15 is a method of coating an optical fiber, the method comprising:
coating an outer surface of an optical fiber with a polymerizable material; and
polymerizing the polymerizable material to yield the coated optical fiber comprising a homogeneous polymer coating,
wherein the optical fiber and the homogeneous polymer coating are UV transparent, and a refractive index of the outer surface of the optical fiber or the homogeneous polymer coating is up to 15% less than a refractive index of a core of the optical fiber, and
wherein the coated optical fiber is free of nanoparticles.

Embodiment 16 is a method of embodiment 15, wherein a refractive index of the UV transparent polymer coating is up to 15% less than the refractive index of the core the optical fiber.

Embodiment 17 is a method of embodiment 15 or 16, further comprising texturing the outer surface of the optical fiber before coating the outer surface.

Embodiment 18 is a method of embodiment 17, wherein texturing the surface comprises chemically or mechanically texturing the surface.

Embodiment 19 is a method of embodiment 17 or 18, wherein texturing the surface of the optical fiber comprises reducing a refractive index of a portion of the optical fiber within 1 μm to 50 μm of the surface of the optical fiber by up to 15%.

Embodiment 20 is a method of any one of embodiments 17 through 19, wherein mechanically texturing the core comprises creating a roughness on a surface of the optical fiber having a peak to valley distance between about 1 nm and about 100 nm.

Advantages of the optical fibers and systems described herein include the capability to disinfect hard-to-reach areas, such as dead-zones within reaction vessels or storage tanks, and pipes or sections of pipes prone to biofouling and/or undergoing water aging due to poor mixing. Such hard-to-reach areas may be susceptible to nitrification, legionella growth (in cooling towers), or membrane fouling. The fibers and systems are compact, chemical-free, portable, and have a low energy requirement. Applications include fibers and systems for use in disinfection of drinking water and medical devices, industrial processing, and military or space applications.

The details of one or more embodiments of the subject matter of this disclosure are set forth in the accompanying drawings and the description. Other features, aspects, and advantages of the subject matter will become apparent from the description, the drawings, and the claims.

DETAILED DESCRIPTION

The disclosure describes integration of diffuse ultraviolet (UV) light sources with side-emitting optical fibers for delivery of UV light, as well as optical systems including two or more of the side-emitting optical fibers. The diffuse UV light source generates light rays at different angles. The separation distance between the light source and inlet end and surface of the optical fiber is a tunable distance that controls angles of light entering the fiber, above or below the critical angle of the fiber, which influences side emission of light from the optical fiber along its length.

Coupling devices that hold the optical fiber(s) at a fixed separation distance from the diffuse light source align the optical fiber axis perpendicular to the center of the diffuse light source. UV transparent polymers or other fixatives are selected to secure the optical fibers within the coupling device. A UV transparent polymer used to secure optical fibers in coupling devices typically have a refractive index less than (e.g., up to 15% less than) that of the optical fiber core material. In one example, the optical fiber is a high hydroxyl content (high-OH) solarized glass with refractive index of about 1.5, and the UV transparent polymer has a refractive index of about 1.35.

The optical fibers are flexible and have a diameter of less than about 1 mm (e.g., about 100 μm to about 500 μm). Each optical fiber is coated with a homogeneous UV-transparent polymer. The homogenous UV transparent polymer can have a refractive index up to 15% less than a refractive index of a core of the optical fiber. In one example, the optical fiber material is a high-OH solarized glass with refractive index of about 1.5, and the UV transparent polymer has a refractive index of about 1.35.

In some implementations, an outer surface of the optical fiber is textured. The texturing can include chemical or mechanical texturing to induce light scattering. Chemical surface texturing yields a refractive index at a surface of the optical fiber (e.g., <1 μm from the surface) that is less than (e.g., up to 15% less than) that of an inner portion of the optical fiber (e.g., a core of the optical fiber, or a portion at a center of the optical fiber along its length). Mechanical texturing can induce surface roughness and create roughness defects on an outer surface of the optical fiber having a peak to valley distance between 1 nm and 100 nm. In one example, sub-micron texturing along the surface of solarized glass optical fibers is added during manufacturing to intentionally scatter light that enters the fiber at less than the critical scattering angle. An example of chemical texturing on the optical fiber surface involves changing the surface porosity, crystallinity, or oxygen surface groups such that the refractive index of an outer surface of the optical fiber is up to 15% less than that of a core of the optical fiber. The refractive index of an outer surface of the optical fiber controlled by chemical texturing can be used as a tunable parameter to vary the light scattering properties of the fiber. Varying the surface roughness modulates the incident light angle inside the optical fiber and creates more side emission of UV-C light that leaves the fiber. This phenomenon can be understood based on random changes in angle of each light ray inside the optical fiber.

The optical fibers are coated with a homogeneous UV transparent polymer. As used herein, a material that is "UV transparent" in a selected wavelength range typically has an average percent transmission of least 80%, at least 85%, at least 90%, or at least 95% over the selected wavelength range. Suitable examples of homogeneous UV transparent polymers include fluorinated polymers (e.g., CYTOP). The homogeneous UV transparent polymer is free of inhomogeneities such as nanoparticles. The homogeneous UV transparent polymer protects the optical fiber from physical damage and facilitates bendability of the optical fiber.

The UV light is typically UV-C light, having a wavelength in a range between about 220 nm and about 280 nm. The side-emitting optical fibers are configured to achieve UV-C side emission.

A light-emitting diode (LED) (e.g., a UV-C LED) with a diffuse light source emission profile is operably coupled to a side-emitting optical fiber or an optical system including a plurality of side-emitting optical fibers. Photons emitted from the LED ($I_{LED}$) that enter the optical fiber ($I_0$) can be transmitted ($I_T$) through the optical fiber core by internal reflection, absorbed ($I_a$) by the core or cladding materials, or side emitted ($I_S$) by scattering of the optical fiber as described by Equation 1.

$$I_0 = I_T + I_a + I_S \qquad (1)$$

The side-emitting optical fiber or fibers are typically placed in a vessel (e.g., a reactor or a conduit) containing a fluid, and configured to deliver UV-C light to an interior of the vessel, thereby controlling biofilms or inactivating microorganisms in the vessel.

EXAMPLES

Commercially available optical fibers having a diameter of 500 µm were coated with the fluorinated polymer CYTOP. The coating material was homogeneous (i.e., free of nanoparticles), and no ionic strength treatment was implemented, using a dip-coating batch or drop-tower continuous production process. Light measurements were made using a spectrophotoradiometer (Avantes, Louisville, CO, AvaSpec-2048L, calibration: 200-1100 nm).

Figure 1:
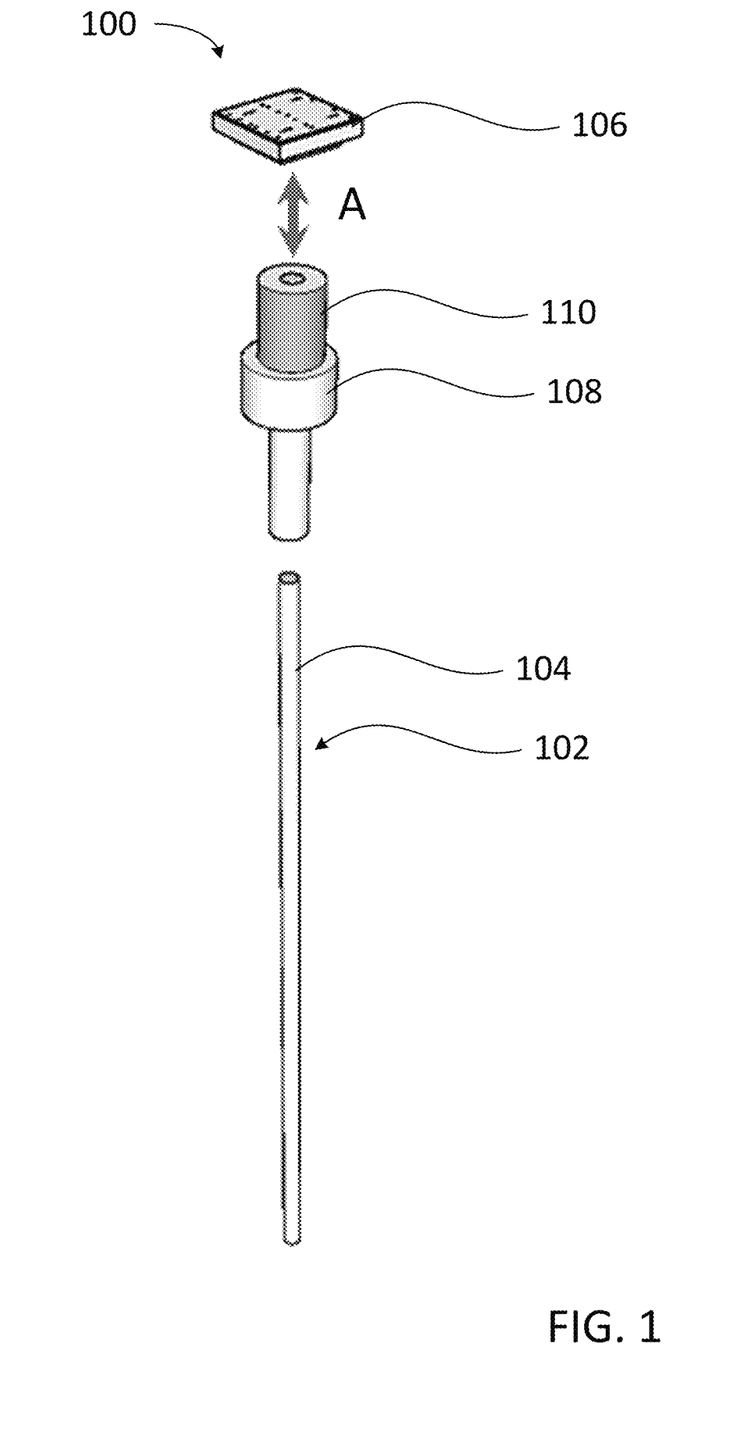
FIG. 1 depicts a light source optically coupled to a textured, polymer coated side-emitting optical fiber through a subminiature version A (SMA) connector.

FIG. 1 is an exploded view of an integrated light source 100 that generates ultraviolet-C (UV-C) side emission from an optical fiber. A side-emitting optical fiber 102 includes a UV transparent optical fiber core with a textured exterior surface 104 that is coated with a homogeneous UV-C transparent polymer. The side-emitting optical fiber 102 is optically coupled to the diffuse light source 106 (e.g., 60 mW 265 nm UV-C LED; Klaran, NY) using a metallic SMA optical fiber ferrule connector 108. The side-emitting optical fiber 102 is held in place by UV transparent polymer 110 (e.g., a UV-C transparent polymer such as CYTOP), positioned in connector 108. UV transparent polymer 110 optically couples optical fiber 102 to light source 106. In some cases, UV transparent polymer 110 secures optical fiber 102 to light source 106. "A" represents the distance between a proximal end of side-emitting optical fiber 102 and a surface of light source 106 through which light travels from the light source to the optical fiber. That is, "A" is the separation distance between an end of optical fiber 102 and light source 106. Optical fiber 102 and light source 106 can be in direct contact (A=0) or can be separated by a distance up to 1 mm or up to 2 mm. Although not depicted in FIG. 1, one or more additional optical fibers can be coupled along with optical fiber 102 to light source 106.

Figure 2:
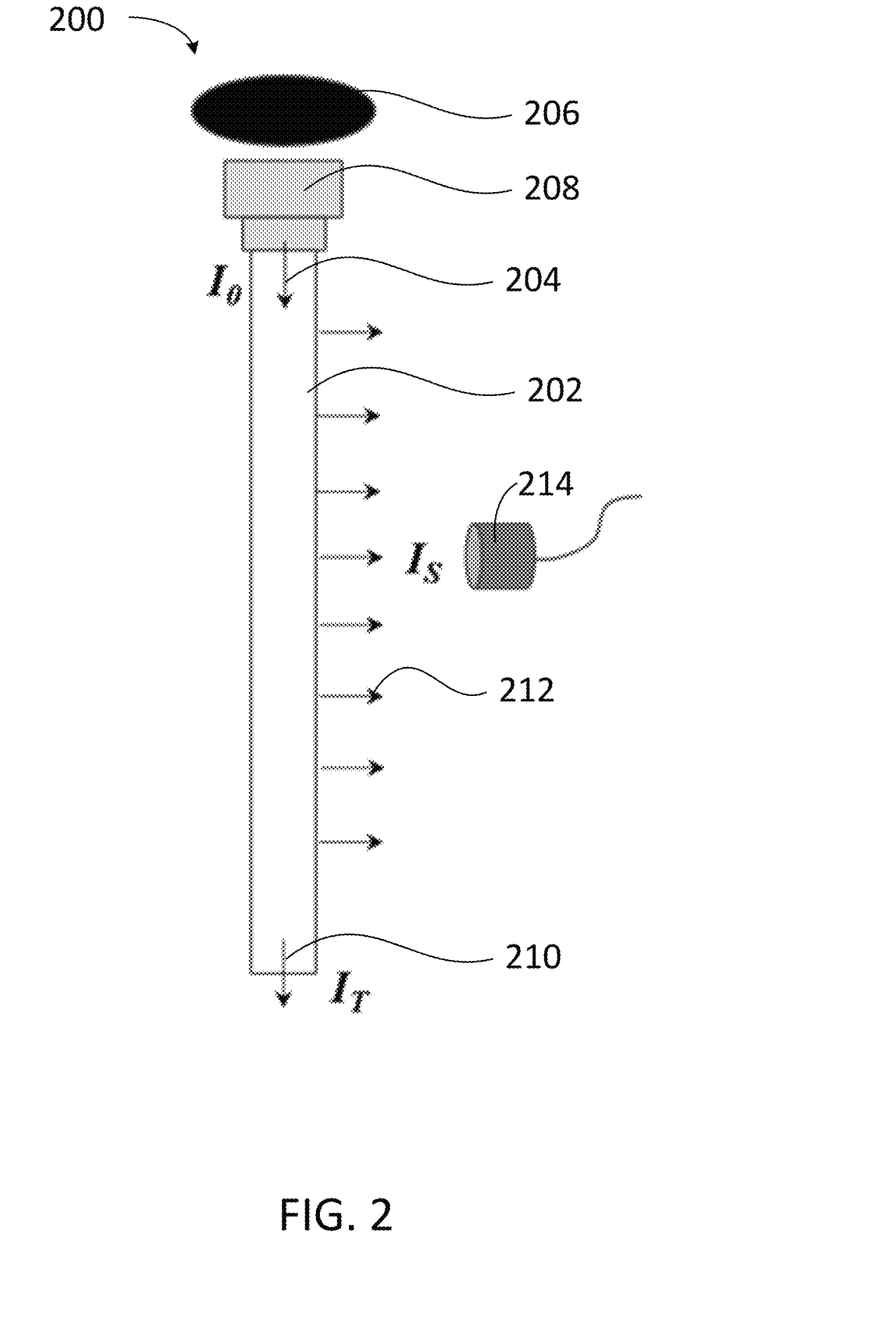
FIG. 2 depicts an apparatus for measuring intensity (μW/cm$^2$) of light launched into an optical fiber ($I_O$) from a diffuse LED light source, light intensity transmission ($I_T$), and light intensity side-emission ($I_S$) for a continuously side-emitting optical fiber.

FIG. 2 shows apparatus 200 for taking measurements of side-emitted photons along the length of the side-emitting optical fiber 202 up to 10 cm perpendicular to the central axis of the fiber. Photons 204 ($I_0$) are emitted from the LED 206 that enter the optical fiber 202 through the SMA connector 208. Photons 210 ($I_T$) are transmitted through the optical fiber core by internal reflection. Photons 212 ($I_S$) are side emitted by scattering of the side-emitting optical fiber 202, as described by Equation 1. The sensor tip 214 of the spectrophotoradiometer is placed normal to the central axis of the side-emitting optical fiber 202. Only photons 212 that are side emitted ($I_S$) are measured by the sensor, and the flux is obtained by integrating the output spectrum.

Figure 3:
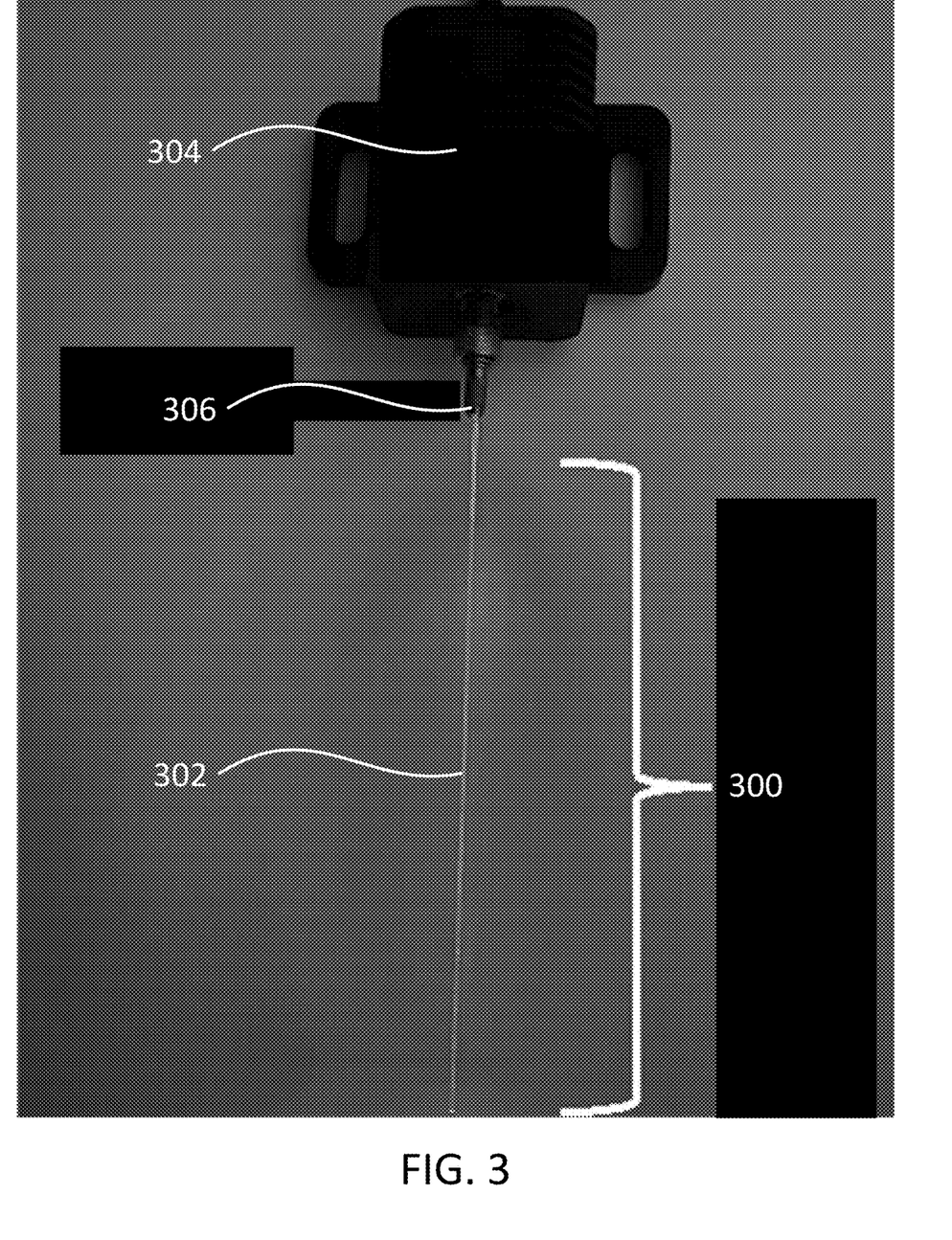
FIG. 3 is a photographic example of an approximately 10 cm long 500-μm diameter side-emitting optical fiber during use.

FIG. 3 is a photograph that shows side-emission of light 300 along the length of the side-emitting optical fiber 302, which can vary from 5 cm or less to 50 cm or greater in length. The amount of side-emitted light 300 and length of side-emitting optical fiber 302 that can effectively emit light is controlled by the light intensity of the LED 304, diffuse emission profile of the LED 304, separation distance between the LED 304 and SMA connector 306, and diameter of the side-emitting optical fiber 302.

Figure 4A:
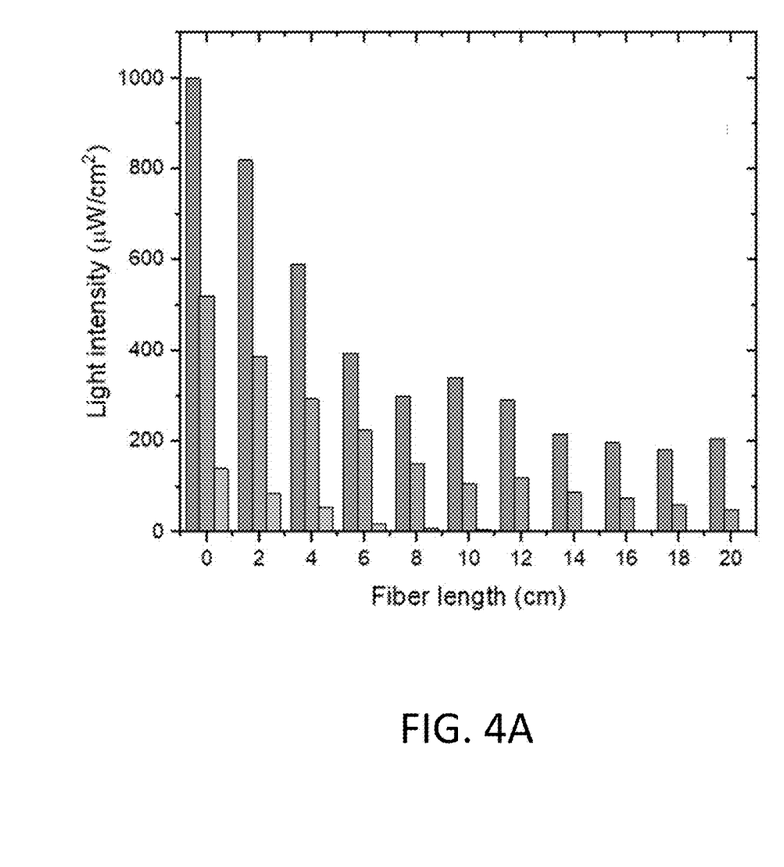
FIG. 4A shows side-emission of UV-C light ($I_S$, μW/cm$^2$) measured along 20 cm optical fibers with a 0 mm separation distance between a diffuse LED light source and an entrance to the optical fiber secured in a SMA connector with a UV-C transparent polymer for three different optical fiber diameters.
Figure 4B:
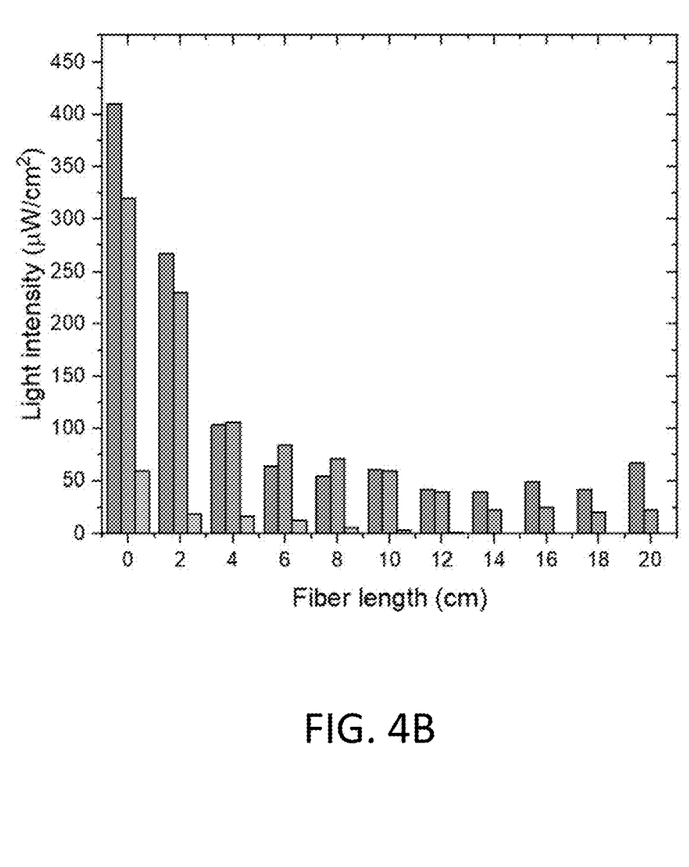
FIG. 4B shows measured side-emission of UV-C light ($I_S$, μW/cm$^2$) measured along 20 cm optical fibers with a 1 mm separation distance between the diffuse LED light source and the entrance to the optical fiber secured in a SMA connector with UV-C transparent polymer for three different optical fiber diameters.

FIG. 4A shows the side emitted light intensity as a function of fiber length for three fiber diameters at approximately 0 mm separation distance between the LED light source and the polished-end input of the side-emitting optical fiber. The fiber diameters at each measured fiber length are 1000 µm (left bar), 500 µm (middle bar), and 250 µm (right bar). FIG. 4A shows that side emission of the coated, textured side-emitting fiber increases with increasing optical fiber diameter. FIG. 4B shows the side-emitted light intensity when the separation distance between the LED light source and the polished-end input of the side-emitting optical fiber is 1 mm. The fiber diameters at each measured fiber length are 1000 µm (left bar), 500 µm (middle bar), and 250 µm (right bar).

Figure 5A:
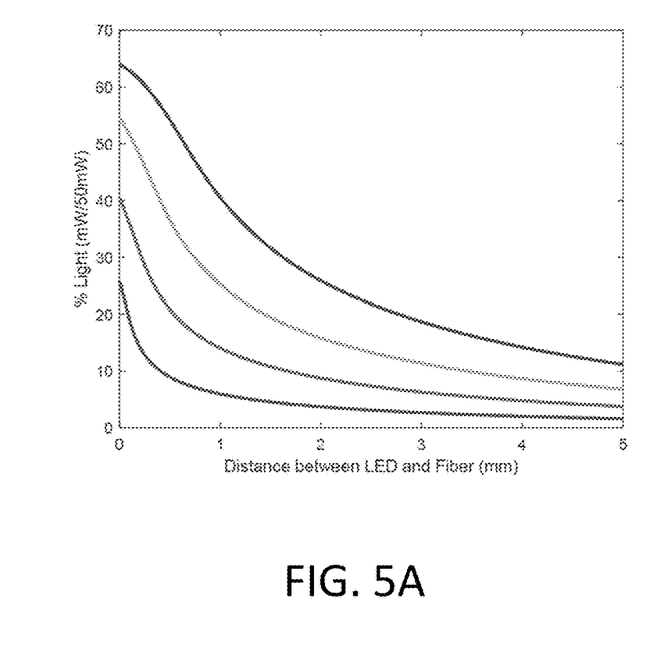
FIG. 5A shows modeling results for LED light that enters side-emitting optical fibers ($I_O$) as a function of separation distance between the LED and SMA connector input for four diameters of optical fibers.
Figure 5B:
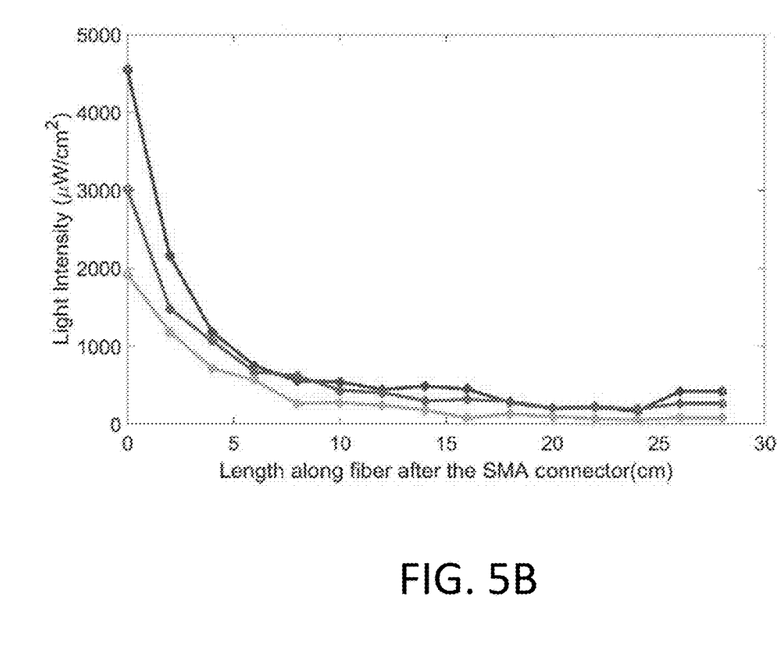
FIG. 5B shows simulated side emission of light ($I_S$) along the length of three diameters of optical fibers at a separation distance of 1 mm between the LED and the SMA connector input.

FIG. 5A shows simulated light intensity entering the fiber ($I_0$) as a function of separation distance between the LED and optical fiber for four diameters of optical fiber. The curves, top to bottom, are simulations for fibers with diameters of 1000 µm, 500 µm, 250 µm, and 100 µm, respectively. Increasing the separation distance or decreasing the fiber diameter reduces $I_0$, but the shape of the curves are non-linear and demonstrate the net impact of how diffuse light ray patterns impact angles of light entering the optical fiber. FIG. 5B shows simulated side emission of light ($I_S$) along the length of three diameters of optical fibers at a separation distance of 1 mm between the LED and the SMA where the light enters the optical fiber. The diameters of the optical fibers are 1000 µm, 500 µm, 250 µm, top to bottom. Tuning the separation distance influences the amount of light above, at or below the critical angle for the optical fiber and consequently influences the amount of light available for side-emission along the length of the optical fiber. Model simulation data in FIG. 5B show greater side-emission of UV-C light ($I_S$) for larger diameter optical fibers. Simulation data in FIG. 5B show the same trends as experimental data in FIG. 4.

Figure 6:
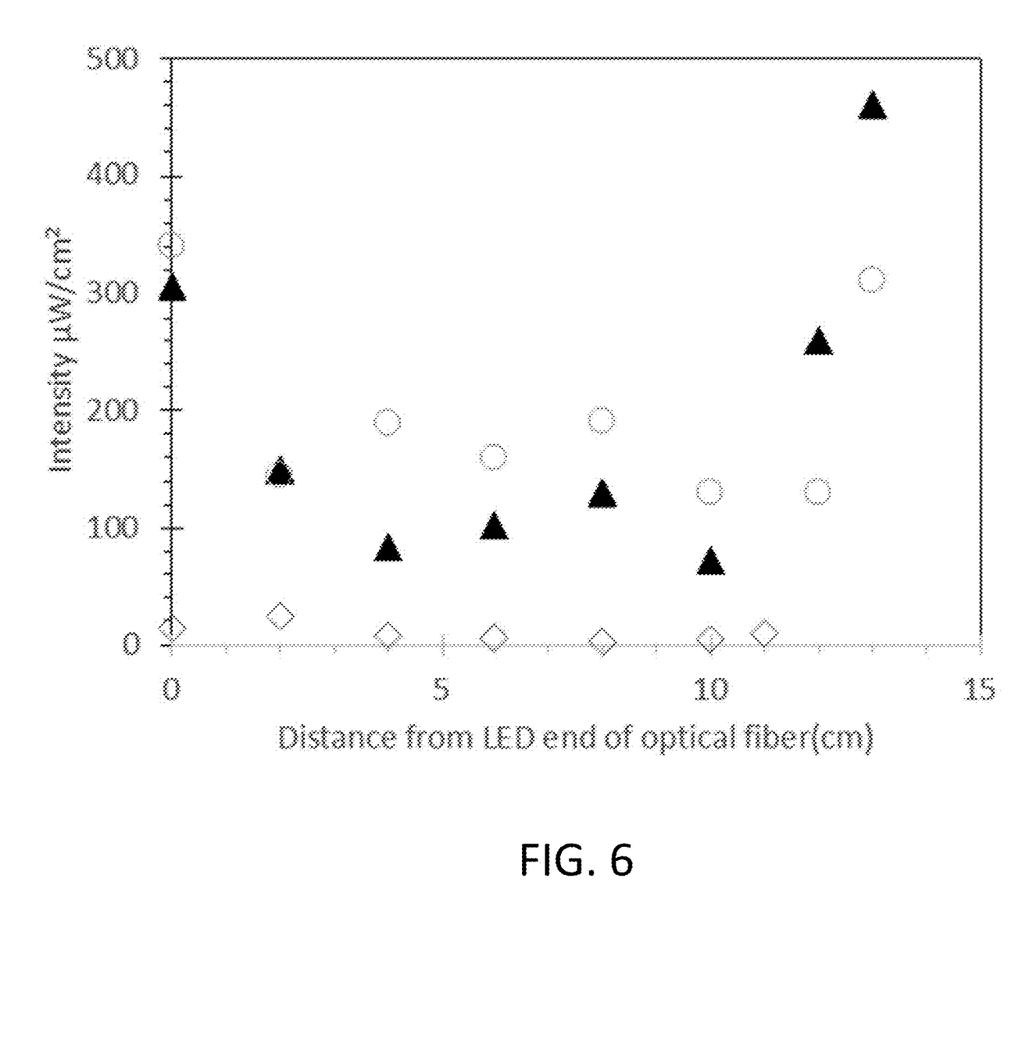
FIG. 6 shows the intensity of side-emitted light from an optical fiber coated with a conventional epoxy (diamonds), the UV-C transparent polymer CYTOP (triangles), and no coating (circles.)

FIG. 6 shows the intensity of side-emitted light from a 1000 µm diameter optical fiber coated with a conventional epoxy (diamonds), the UV-C transparent polymer CYTOP (triangles), and no coating (circles). FIG. 6 shows that UV-C transparent polymer (CYTOP) used within the SMA connector to secure the optical fibers has no adverse impact on side-emitted light ($I_S$) of optical fibers compared with non-coated fiber (circles). A polymer coating allows optical fibers to remain flexible without breaking. Conventional epoxy coating used to secure the optical fiber in the SMA connector prevented almost any side emission of UV-C light (diamonds). In the same experiments, the transmitted light ($I_T$) at the terminal end of the optical fiber (distance of 15 cm from the LED) was nearly equivalent for the fiber with no coating and CYTOP coating. $I_T$ for the conventional epoxy coating was 99% lower for the CYTOP coating and indicated the conventional epoxy coating absorbed much of the UV-C light passing through the length of the optical fiber.

Figure 7A:
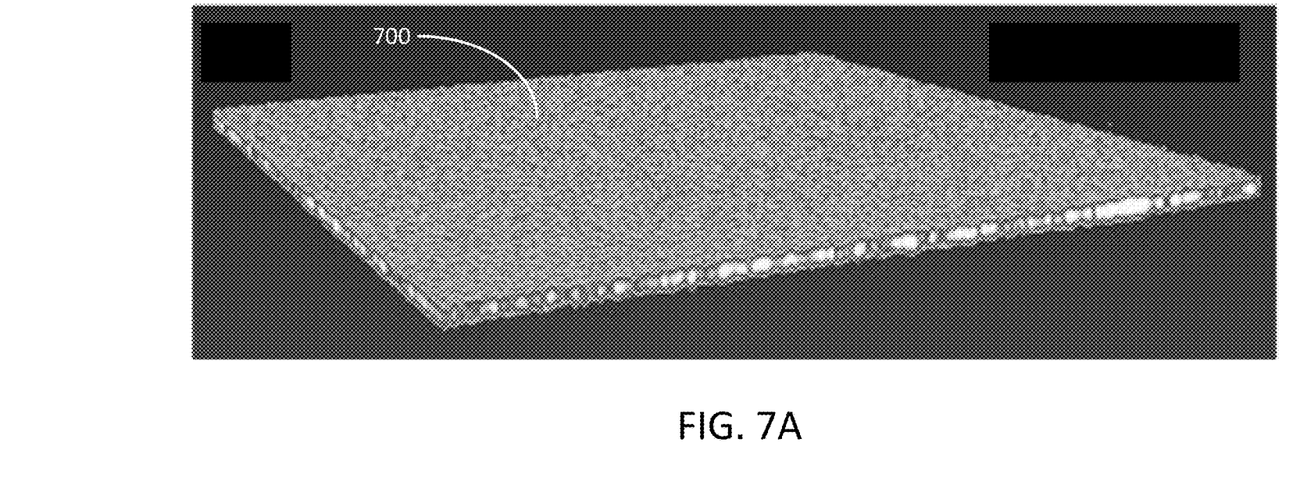
FIGS. 7A and 7B show measurements of biofilm optical density on a metal surface for surface biofilm growth under 275 nm UV-C light irradiated by side-emitting optical fibers and surface biofilm growth without side-emitting optical fibers, respectively.
Figure 7B:
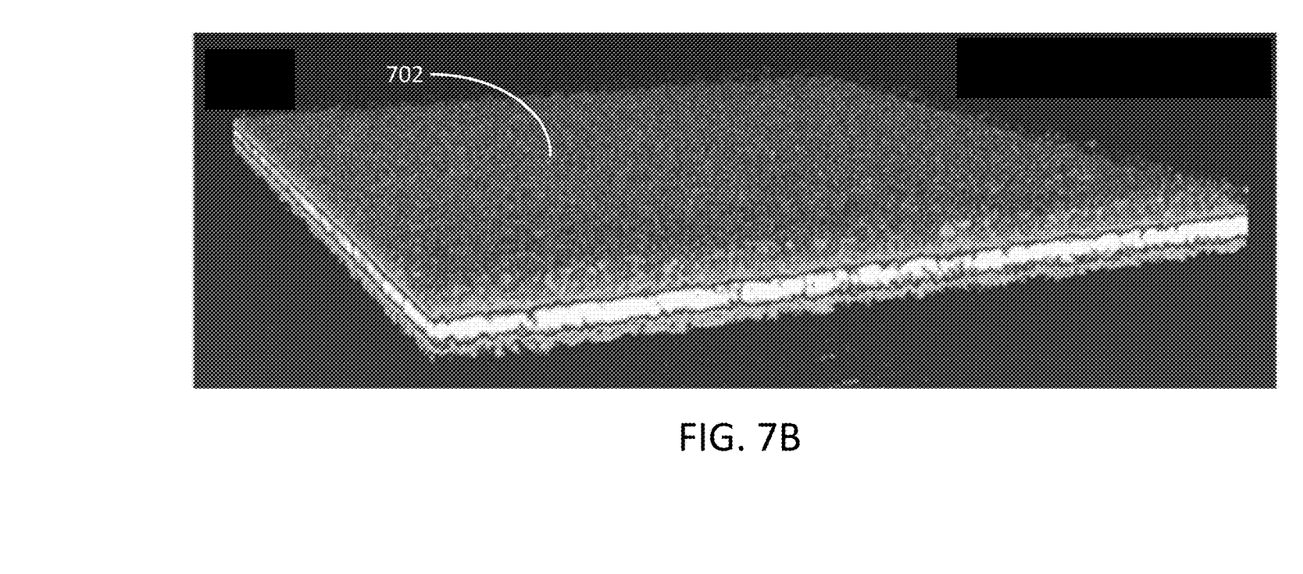

FIGS. 7A and 7B show measurements of biofilm optical density on a metal surface for surface biofilm growth under 275 nm UV-C light irradiated by side-emitting optical fibers and surface biofilm growth without side-emitting optical fibers, respectively. FIGS. 7A and 7B were captured by optical coherence tomography. A single type of microorganism (*Pseudomonas aeruginosa*) was used to form biofilm on the surface. FIG. 7A shows that even under continuous recirculation of high concentration *Pseudomonas aeruginosa* suspensions, there is no biofilm formed on the metal surface 700 under UV-C light irradiated by side-emitting optical fibers. However, FIG. 7B shows that without UV-C irradiation on the surface from side-emitting optical fibers a thick layer of biofilm 702 grew on the surface.

Although this disclosure contains many specific embodiment details, these should not be construed as limitations on the scope of the subject matter or on the scope of what may be claimed, but rather as descriptions of features that may be specific to particular embodiments. Certain features that are described in this disclosure in the context of separate embodiments can also be implemented, in combination, in a single embodiment. Conversely, various features that are described in the context of a single embodiment can also be implemented in multiple embodiments, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular embodiments of the subject matter have been described. Other embodiments, alterations, and permutations of the described embodiments are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results.

Accordingly, the previously described example embodiments do not define or constrain this disclosure. Other changes, substitutions, and alterations are also possible without departing from the spirit and scope of this disclosure.

What is claimed is:

1. A coated optical fiber comprising:
   an optical fiber comprising a core and an outer surface; and
   a homogeneous polymer coating in contact with the outer surface of the optical fiber,
   wherein the optical fiber and the homogeneous polymer coating are UV transparent, and a refractive index of the outer surface of the optical fiber or the homogeneous polymer coating is up to 15% less than a refractive index of the core.

2. The coated optical fiber of claim 1, wherein UV light passing through the optical fiber is scattered by an interface between the outer surface of the optical fiber and the homogenous polymer coating.

3. The coated optical fiber of claim 1, wherein a thickness of the homogeneous polymer coating is between about 10 µm and about 100 µm.

4. The coated optical fiber of claim 1, wherein the homogeneous polymer coating comprises a fluorinated polymer.

5. The coated optical fiber of claim 1, wherein a refractive index of a portion of the optical fiber within 1 µm of the outer surface of the optical fiber is up to 15% less than the refractive index of the core of the optical fiber.

6. The coated optical fiber of claim 1, wherein the outer surface comprises features having a peak to valley distance between about 1 nm and about 100 nm.

7. A disinfectant system comprising the coated optical fiber of claim 1.

8. An apparatus comprising a light source optically coupled to an end of the coated optical fiber of claim 1.

9. The apparatus of claim 8, wherein the light source comprises a light-emitting diode (LED).

10. The apparatus of claim 9, wherein the light source comprises a UV-C LED with a diffuse, non-collimated, light emission pattern.

11. The apparatus of claim 8, wherein the light source is thermally coupled to a heat sink.

12. The apparatus of claim 8, wherein the light source and the end of the optical fiber are separated by a distance selected to modulate angles of light rays entering the end of the optical fiber from the light source.

13. The apparatus of claim 12, further comprising a UV transparent polymer between the light source and the end of the coated optical fiber, wherein the light source and the coated optical fiber are optically coupled by the UV transparent polymer.

14. The apparatus of claim 13, further comprising one or more additional optical fibers coupled to the light source.

15. A method of coating an optical fiber, the method comprising:
   coating an outer surface of an optical fiber with a polymerizable material; and
   polymerizing the polymerizable material to yield the coated optical fiber comprising a homogeneous polymer coating,
   wherein the optical fiber and the homogeneous polymer coating are UV transparent, and a refractive index of the outer surface of the optical fiber or the homogeneous polymer coating is up to 15% less than a refractive index of a core of the optical fiber, and wherein the coated optical fiber is free of nanoparticles.

16. The method of claim 15, wherein a refractive index of the UV transparent polymer coating is up to 15% less than the refractive index of the core the optical fiber.

17. The method of claim 15, further comprising texturing the outer surface of the optical fiber before coating the outer surface.

18. The method of claim 17, wherein texturing the surface comprises chemically or mechanically texturing the surface.

19. The method of claim 17, wherein texturing the surface of the optical fiber comprises reducing a refractive index of a portion of the optical fiber within 1 μm to 50 μm of the surface of the optical fiber by up to 15%.

20. The method of claim 17, wherein mechanically texturing the core comprises creating a roughness on a surface of the optical fiber having a peak to valley distance between about 1 nm and about 100 nm.

21. The method of claim 17, further comprising optically coupling the coated optical fiber to a light source with a UV transparent polymer.

22. The method of claim 21, wherein a separation distance between an end of the coated optical fiber and the light source is up to 2 mm.

\* \* \* \* \*